(12) United States Patent
Sybert

(10) Patent No.: US 7,785,353 B2
(45) Date of Patent: Aug. 31, 2010

(54) INTEGRAL, ARTICULATED, PEDICLE SCREW AND LONGITUDINAL MEMBER FOR SPINAL OSTEOSYNTHESIS

(75) Inventor: Daryl R. Sybert, New Albany, OH (US)

(73) Assignee: Syberspine Limited, New Albany, OH (US)

( * ) Notice: Subject to any disclaimer, the term of this patent is extended or adjusted under 35 U.S.C. 154(b) by 1168 days.

(21) Appl. No.: 11/049,907

(22) Filed: Feb. 2, 2005

(65) Prior Publication Data

US 2006/0195086 A1     Aug. 31, 2006

(51) Int. Cl.
    *A61B 17/70*  (2006.01)
(52) U.S. Cl. ...................................................... 606/272
(58) Field of Classification Search ............. 606/60–61, 606/72–73, 250, 253, 260, 265, 301, 305, 606/306, 266; 623/17.11, 17.14; 403/53, 403/57
    See application file for complete search history.

(56) References Cited

U.S. PATENT DOCUMENTS

| | | | |
|---|---|---|---|
| 3,795,922 A | 3/1974 | Herbert et al. | |
| 3,837,008 A | 9/1974 | Bahler et al. | |
| 4,106,128 A | 8/1978 | Greenwald et al. | |
| 4,827,918 A | 5/1989 | Olerud | |
| 4,887,596 A | 12/1989 | Sherman | |
| 4,946,458 A | 8/1990 | Harms et al. | |
| 5,002,542 A | 3/1991 | Frigg | |
| 5,047,029 A | 9/1991 | Aebi et al. | |
| 5,062,730 A * | 11/1991 | Tomii et al. ................... | 403/57 |
| 5,129,900 A | 7/1992 | Asher et al. | |
| 5,176,680 A | 1/1993 | Vignaud et al. | |
| 5,282,862 A | 2/1994 | Baker et al. | |
| 5,312,404 A | 5/1994 | Asher et al. | |
| 5,324,235 A * | 6/1994 | Tomii et al. .................. | 464/136 |
| 5,486,174 A | 1/1996 | Fournet-Fayard et al. | |
| 5,628,740 A | 5/1997 | Mullane | |
| 6,132,467 A | 10/2000 | Keller | |
| 6,309,391 B1 | 10/2001 | Crandall et al. | |
| 6,478,798 B1 * | 11/2002 | Howland ...................... | 606/61 |
| 2003/0105460 A1 * | 6/2003 | Crandall et al. ............... | 606/61 |
| 2004/0039384 A1 * | 2/2004 | Boehm et al. ................. | 606/61 |
| 2006/0036244 A1 * | 2/2006 | Spitler et al. ................. | 606/61 |
| 2006/0106380 A1 * | 5/2006 | Colleran et al. ............... | 606/61 |

* cited by examiner

*Primary Examiner*—Eduardo C Robert
*Assistant Examiner*—Elana B Fisher
(74) *Attorney, Agent, or Firm*—Frank H. Foster; Kremblas & Foster

(57) ABSTRACT

A pedicle screw is pre-connected to a longitudinal member by an articulation joint. The articulation range is through an angle extending at least from a 90° angle between the longitudinal axis of the pedicle screw and the longitudinal axis of the longitudinal member to an angle sufficiently near a coaxial orientation between those longitudinal axes to permit the first pedicle screw to be screwed into a pedicle of a first vertebra with the longitudinal member attached to the first pedicle screw. A lock fixes the longitudinal member to the first pedicle screw in a selected orientation. A second pedicle screw has an anchor joint with a lock for receiving and being fixed to the longitudinal member after the longitudinal member is rotated into engagement with the anchor joint. The pre-connection with sufficient articulation eliminates the need to connect the longitudinal member to one of the pedicle screws through an incision and assures proper alignment of any bend placed in the longitudinal member.

2 Claims, 6 Drawing Sheets

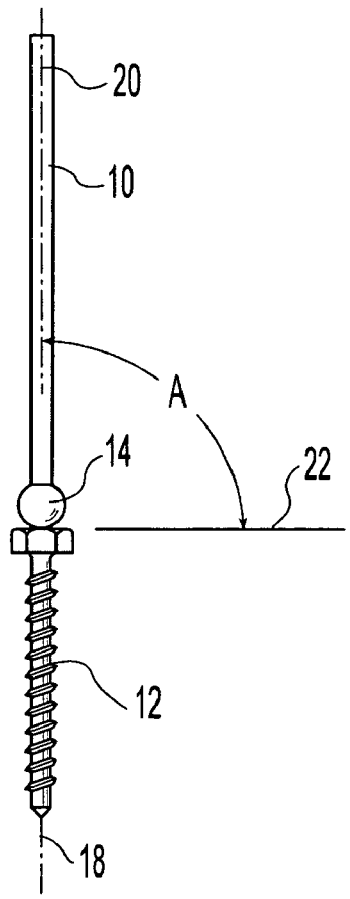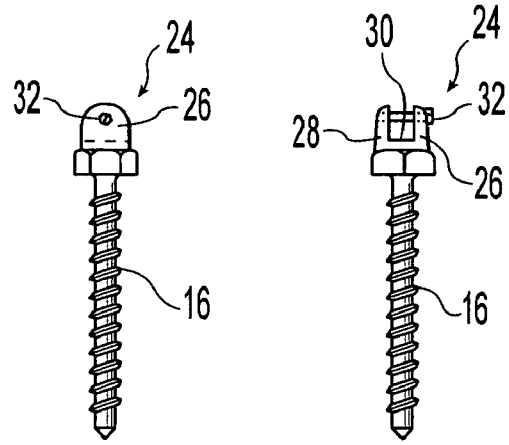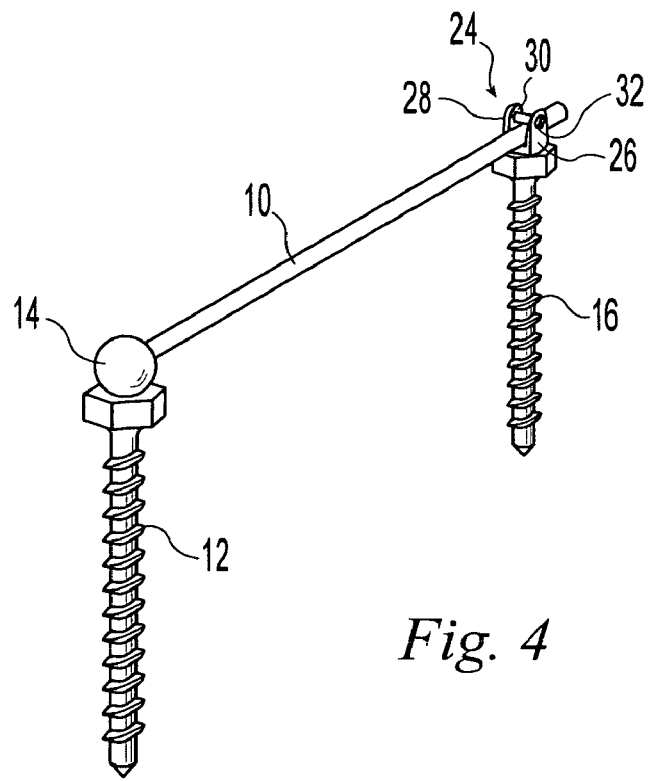
Fig. 1
Fig. 2
Fig. 3
Fig. 4

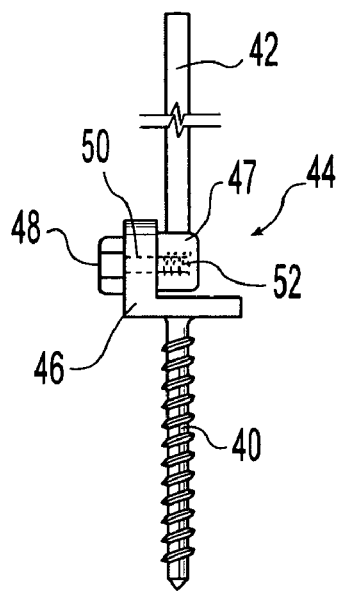
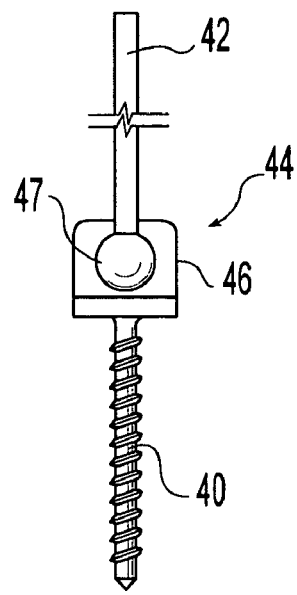
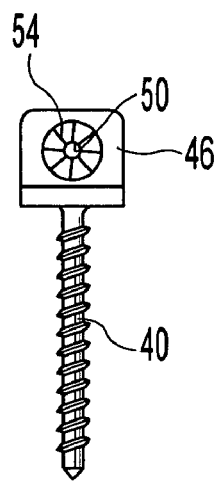
*Fig. 5*  *Fig. 6*  *Fig. 7*
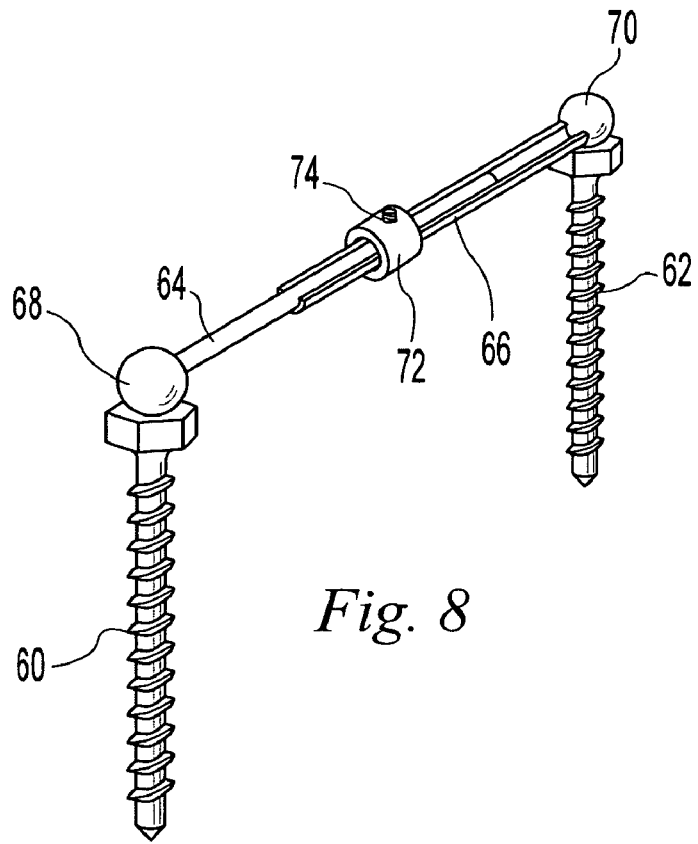
*Fig. 8*

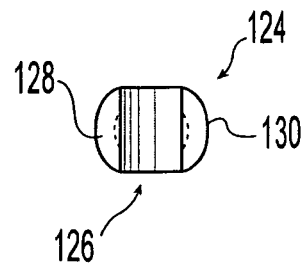
Fig. 15
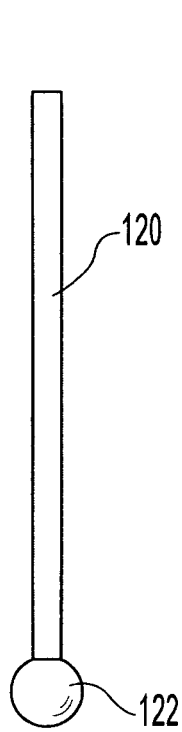
Fig. 14
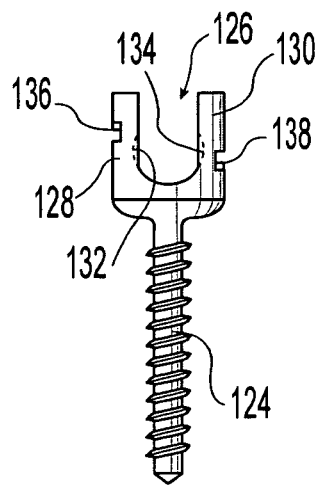 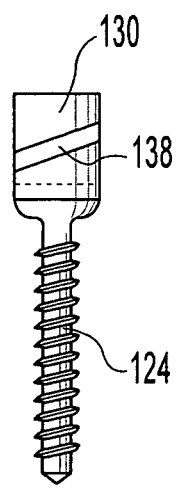
Fig. 16   Fig. 17
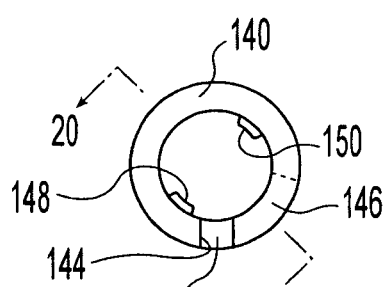
Fig. 18
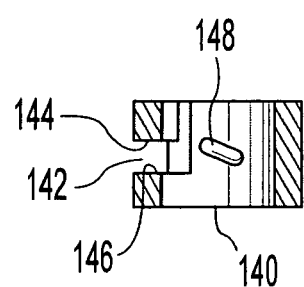
Fig. 20
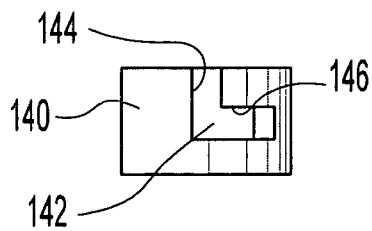
Fig. 19

INTEGRAL, ARTICULATED, PEDICLE SCREW AND LONGITUDINAL MEMBER FOR SPINAL OSTEOSYNTHESIS

BACKGROUND OF THE INVENTION

1. Field of the Invention

This invention relates generally to the field of orthopedic spine surgery and more particularly to spinal osteosynthesis structures and methods that are particularly useful for performing a minimally invasive, lumbar spine fusion or other spinal fixation.

2. Description of the Related Art

The prior art teaches a variety of structures and methods for treating one or more degenerated, deformed or damaged vertebral stages of a patient's spinal column by means of internal spinal fixation. Typically, this involves the attachment of a spinal implant system to provide a support structure that is attached to two or more adjacent vertebrae to support and stabilize the vertebrae in a stationary relationship relative to each other. More specifically, pedicle screws are fastened into the pedicles of the vertebrae and the screws are joined together by a rigid member, such as a spinal support rod, plate or other structural assembly that extends in a cranial-caudal direction between and attached to the pedicle screws. The rigid member that extends between the pedicle screws is commonly referred to as the "longitudinal member" because it extends generally parallel to the longitudinal axis of the spine.

Surgical techniques have progressively improved to require smaller and smaller incisions. While this is a benefit to the patient's comfort and healing process, it also makes the surgeon's task more difficult because of the reduced space that is available to perform the necessary manipulations. With prior art devices and procedures, the pedicle screws are first installed and then the longitudinal member is installed by attaching it to each pedicle screw. However, to install the longitudinal member after the pedicle screws have been implanted, the surgeon must find the small pedicle screws through the incision, manipulate the longitudinal member through the incision into attachment to each pedicle screw, align any bend in the longitudinal member into the proper plane and then tighten the longitudinal member to each pedicle screw to prevent any movement or articulation. When successfully accomplished, the longitudinal member is retained in a fixed, stationary relationship to each screw. However, the pedicle screws are difficult to find through the incision and it is difficult, when working through a small incision and deeply through retracted muscles, to manipulate the longitudinal member into proper alignment and engagement with each pedicle screw and to attach and tighten the longitudinal member to the screws.

It is therefore an object and feature of the invention to provide a structure and a method that reduce the difficult manual manipulations which the surgeon must perform in order to successfully implant the support structure that retains the adjacent vertebrae in a stationery relative relationship.

BRIEF SUMMARY OF THE INVENTION

The apparatus of the invention has a longitudinal member that is attached by an articulation joint to a first pedicle screw. The articulation range of the articulation joint is through an angle extending at least from a 90° angle between the longitudinal axis of the pedicle screw and the longitudinal axis of the longitudinal member to an angle sufficiently near a coaxial orientation between said longitudinal axes to permit the first pedicle screw to be screwed into a pedicle of a first vertebra with the longitudinal member attached to the first pedicle screw. The articulation joint has a lock for securing the longitudinal member to the first pedicle screw in a selected orientation and for preventing relative articulation away from that orientation. A second pedicle screw, for attachment in a pedicle of a second vertebra, has an anchor joint for receiving and attaching to the longitudinal member after the longitudinal member is rotated into engagement with the anchor joint.

The method of the invention involves first, pre-connecting a first pedicle screw in articulated attachment to a longitudinal member before installing the first pedicle screw in the pedicle of a vertebra. This would ordinarily be done by a manufacturer. The pedicle screw is installed in a vertebral pedicle while the longitudinal member is in articulated attachment to the first pedicle screw. At least a second pedicle screw is also installed in a pedicle of another vertebra. The longitudinal member is then articulated into engagement with the second pedicle screw and locked in a selected orientation relative to each pedicle screw for preventing any subsequent relative articulation away from that orientation.

The most important features of the invention are the pre-connection of one pedicle screw to the longitudinal member, the ability of the longitudinal member to be articulated so the attached pedicle screw can be implanted with the longitudinal member attached, the ability of the longitudinal member to then be articulated down to a second pedicle screw, the ability of the second pedicle screw to receive and securely engage the longitudinal member as it is rotated into position and the ability to lock the longitudinal member to each pedicle screw in a selected relative orientation. The invention eliminates the need to connect the longitudinal member to one of the pedicle screws through an incision.

BRIEF DESCRIPTION OF THE SEVERAL VIEWS OF THE DRAWINGS

FIG. 1 is a view in side elevation of a first pedicle screw in articulated attachment to a longitudinal member and embodying the invention.

FIG. 2 is a view in side elevation of a second pedicle screw for being fixed to the longitudinal member of FIG. 1.

FIG. 3 is a view in front elevation of the pedicle screw of FIG. 2.

FIG. 4 is a view in perspective of the pedicle screws and longitudinal member of FIGS. 1-3 assembled in their implanted connection.

FIG. 5 is a view in front elevation of an alternative embodiment of the invention.

FIG. 6 is a view in side elevation of the embodiment of FIG. 5.

FIG. 7 is a view in side elevation of pedicle screw component of the embodiment of FIG. 5.

FIG. 8 is a view in perspective of another alternative embodiment of the invention.

FIGS. 9 and 1 are medial views and FIGS. 10 and 12 are posteroanterior views.

FIG. 14 is view in side elevation of a longitudinal member component of an alternative embodiment of the invention.

FIG. 15 is a top plan view of a pedicle screw component for use with the component of FIG. 14.

FIG. 16 is a front elevation view of the pedicle screw component of FIG. 15.

FIG. 17 is a view in side elevation of the pedicle screw component of FIG. 15.

FIG. 18 is a top plan view of a collar component for use with the components illustrated in FIGS. 14-17.

FIG. 19 is a front elevation view of the collar component of FIG. 18.

FIG. 20 is a view in section taken substantially along the line 20-20 of FIG. 18.

Figure 9:
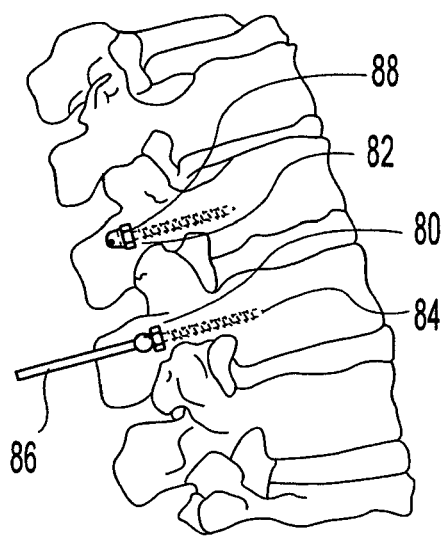
FIGS. 9-12 illustrate the method for implanting two pedicle screws and a bridging longitudinal member to a spine in accordance with the invention.
Figure 10:
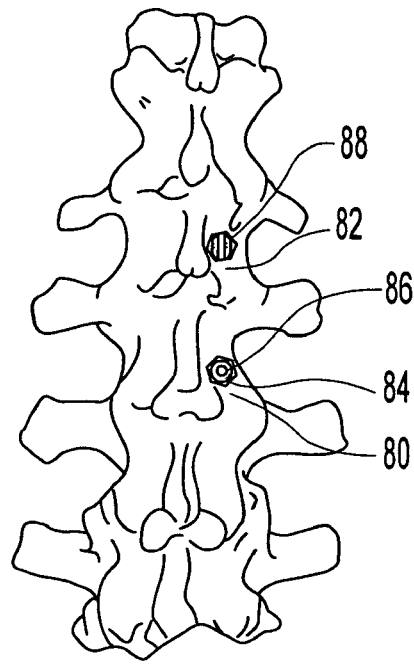
Figure 11:
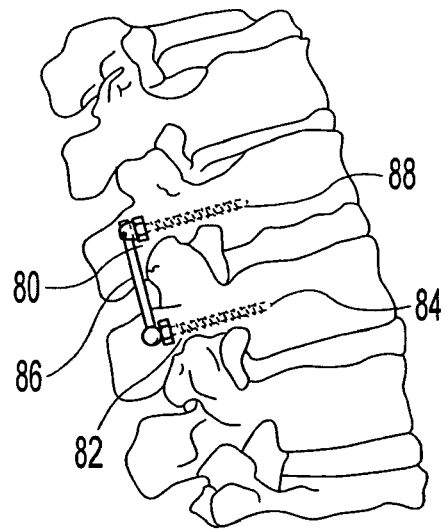
Figure 12:
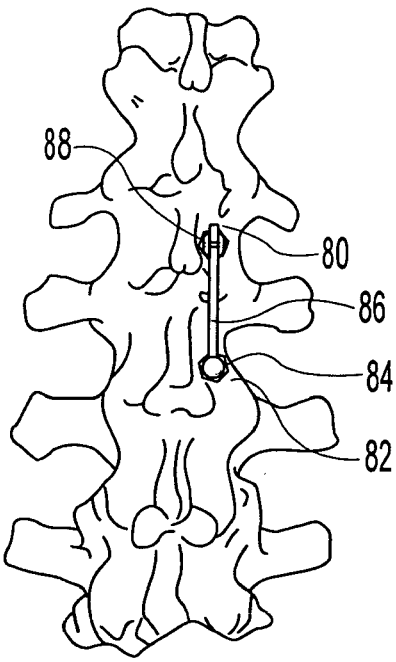

In describing the preferred embodiment of the invention which is illustrated in the drawings, specific terminology will be resorted to for the sake of clarity. However, it is not intended that the invention be limited to the specific term so selected and it is to be understood that each specific term includes all technical equivalents which operate in a similar manner to accomplish a similar purpose. For example, the word connected or term similar thereto are often used. They are not limited to direct connection, but include connection through other elements where such connection is recognized as being equivalent by those skilled in the art.

DETAILED DESCRIPTION OF THE INVENTION

FIGS. 1-4 illustrate a spinal implant embodying the invention for being surgically attached to and supporting at least two adjacent spinal vertebrae in stationery relationship. A longitudinal member 10 is connected in articulated attachment to a first pedicle screw 12 by means of an articulation joint 14. The illustrated longitudinal member 10 is a bar but, as known to those skilled in the art, the longitudinal member can be a plate or other structure for bridging between two or more pedicle screws and rigidly attaching to them. A second pedicle screw 16 is provided for attachment in a pedicle of a second vertebra and is adapted for attachment to the longitudinal member 10. A lock (not visible in FIGS. 1-4) is provided, ordinarily as part of the articulation joint 14, for securing the longitudinal member 14 to the first pedicle screw 12 in a selected orientation in order to prevent relative articulation from that orientation.

The articulation range of the articulation joint 14, that is the angle through which the longitudinal member 10 can move relative to the pedicle screw 12, extends at least from a 90° angle A between the longitudinal axis 18 of the pedicle screw 12 and the longitudinal axis 20 of the longitudinal member 10 to sufficiently near a coaxial orientation between those longitudinal axes to permit the first pedicle screw 12 to be screwed into the pedicle of a first vertebra while the longitudinal member 10 is attached to the first pedicle screw 12. In the embodiment illustrated in FIGS. 1-4, the longitudinal axis of the 20 of the longitudinal member can move through at least 90° from alignment along line 22 to coaxial alignment of the axes as illustrated in FIG. 1.

The articulation joint 14 can be like many of the articulation joints shown in the prior art or subsequently developed. It is illustrated in FIGS. 1-4 diagrammatically or generically as a sphere and therefore its detailed structure is not visible in those Figs. The prior art shows many examples of structures for joining two bodies in an articulated relationship and also many examples of structures for locking the bodies in a selected relative orientation within the limits of the articulation range. They include both structures that permit only 2-dimensional articulation, such as pivoting in the manner of a hinge, and structures that permit 3-dimensional articulation such as U-joints and ball joints, which are preferred because they have more versatility in their available relative orientations. Some articulation joints already used in the surgical field can be used. The present invention is not intended to be limited to particular articulation structures but rather is directed to the articulation range and the relationship between the pedicle screw and the longitudinal member.

The important characteristic of the articulation joint is that it must permit the pedicle screw to be rotated about its longitudinal axis and driven into the pedicle of a vertebra while the longitudinal member is attached to the pedicle screw. The articulation joint must also permit the longitudinal member to thereafter be rotated down generally parallel to the spine and be connected to a second pedicle screw. In other words, the unique structural feature of the invention is that the longitudinal member is articulated so it can pivot sufficiently near alignment with the pedicle screw so that the screw can be inserted with the longitudinal member attached in that orientation and then later the longitudinal member can be pivoted down and connected to at least one other pedicle screw. The longitudinal member may be attached to multiple other pedicle screws, as is sometimes the practice in the art.

Practice or use of the invention also ordinarily involves a second pedicle screw that attaches in a pedicle of a second vertebra and has an anchor joint for receiving and attaching to the longitudinal member after the longitudinal member is rotated into engagement with the anchor joint. The anchor joint of the second pedicle screw should also have a locking structure to fix the longitudinal member in a stationary, spatial relationship with respect to the second pedicle screw. The prior art has many examples of structures for rigidly securing a rod, plate or other bridging support structure to a second body and many such structures can be used to form anchor joints suitable for the invention.

The embodiment of FIGS. 1-4 has an anchor joint 24 that has a pair of upstanding ears 26 and 28. The ears 26 and 28 are spaced apart to form a slot 30. The slot 30 receives the longitudinal member 20 when it is rotated down into the slot 30 from the orientation illustrated in FIG. 1 to the position illustrated in FIG. 4. A small hex head screw 32 is threadedly engaged to a threaded bore in the ear 28 and slidably passes through a smooth bore in the ear 26 so the screw 32 can be tightened and clamp the longitudinal member 20 between the ears 26 and 28 in fixed relationship to the second pedicle screw 16. A substantial variety of other structures can be formed on or attached to the second pedicle screw and used or adapted to attach the second screw to the longitudinal member. Any additional pedicle screws can also be attached to the same longitudinal member by similar anchor joints.

It is desirable that the articulation joints and the anchor joints can be unlocked and disarticulated or disconnected so that, if necessary, a surgeon can later surgically modify the relative orientations between the longitudinal member and any one or more pedicle screws and then lock them in the new relative orientation.

The preferred material from which the components of the invention are formed is stainless steel or titanium, although other surgically implantable materials that have sufficient mechanical strength may also be used.

FIGS. 5-7 show a pedicle screw, articulation joint and longitudinal member embodying the invention. A pedicle screw 40 is attached to a longitudinal member 42 by an articulation joint 44. The articulation joint 44 has an L-shaped bracket 46 fixed to the top of the pedicle screw 40. A rotatable hub 47 is fixed to the longitudinal member 42 and is pivotally attached to the bracket 46 by a hex head screw 48. That hex screw 48 extends through a smooth bore 50 formed through the upstanding portion of the bracket 46 and into threaded engagement in a threaded bore 52 formed in the hub 47. When the hex screw 48 is loose, the hub 47 and the longitudinal member 42 carried by it can be rotated between an angle of about 80° with the axis of the pedicle screw 40 through about 100° of rotation into coaxially alignment with the pedicle screw 40. At any selected angle within this articulation range, the hex screw 48 may be tightened to clamp the hub 47 against the bracket 46 to fix the orientation of the pedicle screw 40 relative to the longitudinal member 42. A series of radial serrations 54 are advantageously formed about the bore 50 to increase the frictional engagement of the hub 47 to the bracket 46. Mating serrations may also be formed about the threaded bore 52 on the face of the hub 47. The combination of the hex screw 48 and its cooperation with the bracket 46 and the hub 47 to clamp them in a fixed relative orientation forms the lock of this embodiment of an articulation joint.

There are many other alternative embodiments, especially for the articulation joints and the anchor joints, that can be used with the invention and only a few examples are given. There are also alternative ways that the basic structure of a pedicle screw that is in articulated attachment to a longitudinal member can be utilized. For example, two pedicle screws can each have both a longitudinal member articulated to it in accordance with the invention and each also have an anchor joint formed on it. These two pedicle screws can both be implanted and then both longitudinal members can be rotated downwardly toward each other until they lie side by side. Each can then be attached to the other pedicle screw by its anchor joint.

Yet another, though similar, embodiment is illustrated in FIG. 8. A pair of pedicle screws 60 and 62 respectively have longitudinal members 64 and 66 attached to them by respective articulation joints 68 and 70. The two longitudinal members, however, are connectible to each other. The embodiment of FIG. 8 accomplishes this by forming one longitudinal member 64 as a rod and the other longitudinal member 66 as a trough that matingly receives the rod shape of the longitudinal member 64. This allows the surgeon to implant both pedicle screws 60 and 62 while their attached longitudinal members 64 and 66 extend coaxially with their respective pedicle screws 60 and 62. Then a collar 72 with a radial, threadedly engaged set screw 74 is slid onto one of the longitudinal member. The surgeon then rotates the longitudinal members into the engagement shown in FIG. 8, slides the collar so it surround the engaging segments of both longitudinal members, and tightens the set screw 74 to fix the two longitudinal members together. Consequently, in this embodiment, the longitudinal member is indirectly attached in fixed engagement with the second pedicle screw by engaging one longitudinal member to the other by means of the collar and the mating receipt of one longitudinal member in the other.

Surgical installation of embodiments of the invention begins with the step of pre-connecting a first one of the pedicle screws in articulated attachment to a longitudinal member before installing the first pedicle screw in the pedicle of a vertebra. This assembly is ordinarily accomplished by the manufacturer prior to delivery of the device although it can be performed by the surgeon or an assistant. Referring to FIGS. 9-12, the surgeon makes a cranial-caudal incision exteriorly of the pedicles 80 and 82 to be joined and approximately the length of the longitudinal member and retracts the skin and muscle. The incision can be a little shorter because the incision can be moved over the spine a limited distance. The surgeon may bend the longitudinal member at a desired angle and then installs the first pedicle screw 84 in a first vertebral pedicle 82 while the longitudinal member 86 is in articulated attachment to the first pedicle screw 84 and most conveniently with the longitudinal member 86 oriented coaxially with the first pedicle screw 84.

An insertion driver (not shown) may be used for rotating the pedicle screw. The insertion driver may be an extra long, hex head, driving socket with an axial passage that has a sufficiently large diameter to receive the entire longitudinal member. Sockets of that type are used by mechanics for turning nuts on screws that protrude a long distance beyond the nut. Alternatively, the insertion driver can be in the nature of an open end or a box wrench.

After installing the first pedicle screw 84, the second pedicle screw 88 is installed in a second vertebral pedicle 80. The longitudinal member 86 is then articulated or rotated into engagement with the second pedicle screw 88. The surgeon then locks the longitudinal member 86 to the pedicle screws 84 and 88 for securing the longitudinal member 86 in a selected orientation relative to the pedicle screws 84 and 88 and preventing articulation away from that orientation.

With the invention, the step of attachment of the longitudinal member to one of the pedicle screws after the pedicle screw is installed is made unnecessary because the longitudinal member is pre-attached to the pedicle screw. Consequently, after the pedicle screw is attached, the longitudinal member is merely folded into the incision and into the anchor joint of second pedicle screw, attached to the second pedicle screw and locked to both pedicle screws. This means one there is one less structure that the surgeon must feed down between the retracted muscles and engage with another structure.

Another advantage of the invention is that, in embodiments where the articulation joint permits only a hinge-like pivoting movement of the longitudinal member but does not permit the longitudinal member to rotate about its longitudinal axis, the surgeon is able to form the bend in the longitudinal member in a selected plane and when the longitudinal member is rotated down to engage the second pedicle screw, the bend will remain in the selected plane. In many prior art structures, the longitudinal member, commonly a rod, is inserted into the surgical opening for attachment to at least two pedicle screws. Consequently, during this insertion the longitudinal member is free to rotate about its longitudinal axis, thus changing the plane of the bend. The surgeon must be careful to rotate the longitudinal member about its longitudinal axis to adjust the bend to align in the desired plane. With embodiments of the invention, this becomes unnecessary because the longitudinal member can not rotate about its longitudinal axis and therefore can not become misaligned.

The prior art shows double jointed pedicle screws but the member that is articulated to the pedicle screw is not a longitudinal member but rather is an extension of the pedicle screw to which other appliances are attached. The prior art also shows longitudinal members in articulated attachment to pedicle screws. However, the longitudinal members of the prior art are attached after implantation of the pedicle screws. The prior art devices do not have the range of articulation of the invention, which is the capability of the pedicle screw and its attached longitudinal members to be articulated sufficiently far from a 90° angle with the pedicle screw and sufficiently close to coaxial alignment with the pedicle screw that the pedicle screw can be installed while the longitudinal member is attached to it. If prior art longitudinal members were attached to the pedicle screw during installation of the pedicle screw and the pedicle screw were tightened into the pedicle, the longitudinal members of the prior art would engage the skin or the incision and would need to be rotated beneath the incision to fully engage the screw. By having the longitudinal member capable of articulating sufficiently near alignment with the screw, that is avoided.

Figure 13:
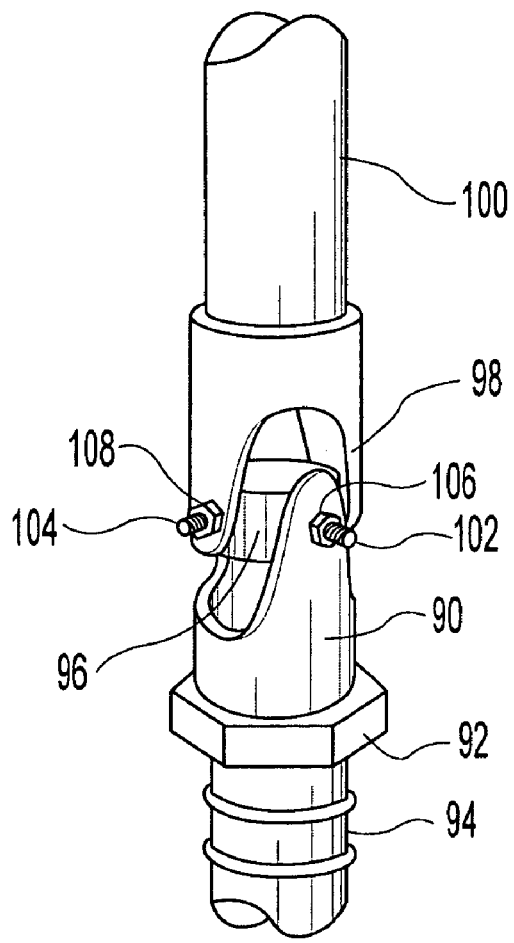
FIG. 13 is a view in perspective of a segment of an alternative embodiment of the invention.

FIG. 13 shows a segment of an alternative embodiment of the invention illustrating an alternative articulation joint. This joint is much like a universal joint. It has a lower yoke 90 fixed to the hex head 92 of a pedicle screw 94. The lower yoke 90 has its two arms pivotally connected to two legs of an intermediate spider 96. An upper yoke 98 has its two arms pivotally connected to the other two legs of the spider 96 and is attached at its opposite end to a longitudinal member 100. The pivots of the spider 96 are formed by four threaded rods 102, 104, and two on the opposite side that are not visible. Each of these four threaded rods are fixed to a different one of the legs of the spider 96 and each rod pivotally extends through a different one of the legs of the yokes 90 and 98. Nuts 106, 108, and two on the opposite side that are not visible, are each threadedly engaged to a different one of threaded rods. Consequently, when the nuts are loosely turned onto the threaded rods, the longitudinal member 100 is free to articulate with respect to the pedicle screw 94. However, when the longitudinal member 100 is articulated to the desired position for attachment to another pedicle screw, each of the nuts can be tightened to retain the longitudinal member 100 against further articulation. Hex head screws can be substituted for the nuts and threaded rods and would be threadedly engaged to threaded bores extending radially into the ends of each of the four legs of the spider.

FIGS. 14-26 illustrate yet another articulation joint for use in embodiments of the invention. FIGS. 14-20 illustrate the unassembled, component parts. FIG. 14 shows a longitudinal member 120 fixed, such as by welding, to a spherical ball 122.

FIGS. 15-17 illustrate a pedicle screw 124 having a saddle 126 formed distally from its threaded end by a pair of upstanding arms 128 and 130. Formed into each interior, centrally facing, planar wall of the arms 128 and 130 is a cavity, 132 and 134 respectively, with a spherical contour dimensioned to matingly receive the exterior surface of the ball 122. The ball 122 is constructed with a diameter slightly greater than the distance between the upstanding arms 128 and 130 but the bottoms of the spherical cavities 132 and 134 are spaced apart a distance substantially equal to the diameter of the ball 122. Consequently, the ball can be pressed between the upstanding arms 128 and 130 to deflect them apart until the ball 122 is received in the cavities. This forms a joint, somewhat like a ball joint, that allows the longitudinal member 120 to be articulated with respect to the pedicle screw 124 but they remain joined by the seating of the ball 122 in the spherically contoured cavities 132 and 134. Inclined grooves 136 and 138 are formed into the exterior, opposite surfaces of the upstanding arms 128 and 130. These oppositely facing grooves 136 and 138 are essentially segments of female screw threads.

FIGS. 18-20 illustrate a collar 140 that matingly but slidably surrounds and engages the exterior surfaces of the upstanding arms 128 and 130. The collar 140 has an L-shaped groove 142 that has an axial segment 144 intersecting a circumferential segment 146. A pair of inclined ridges 148 and 150 project inwardly from the interior surface of the collar 140 in diametrically opposite locations. These ridges 148 and 150 are essentially segments of male threads and are dimensioned to slide within the inclined grooves 136 and 138 formed into the exterior surface of the upstanding arms 128 and 130. Consequently, the collar 140 can be positioned to surround the upstanding arms 128 and 130 and, when rotated through an angle of approximately 80°, will translate axially downwardly and tighten in the manner of a screw.

Figure 21:
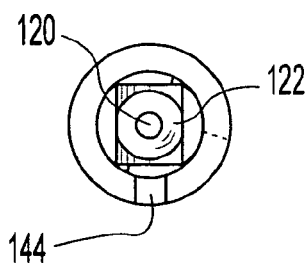
FIG. 21 is a top plan view of the assembled components of FIGS. 14-20 in an initial configuration.
Figure 22:
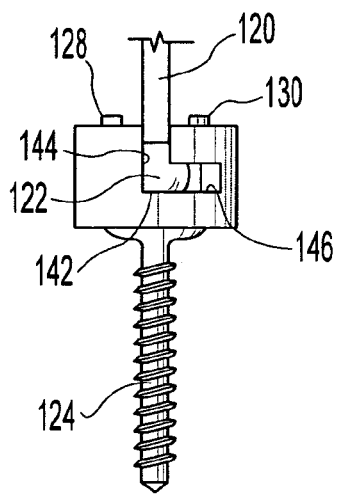
FIG. 22 is a front elevation of the assembled components of FIG. 21.

FIGS. 21 and 22 illustrate the initial assembly. The ball 120 is inserted into the saddle 126 between the upstanding arms 128 and 130 in the manner described above, preferably with the longitudinal member 120 aligned coaxially with the pedicle screw 124. The longitudinal member 120 is inserted through the collar 140 and the collar 140 is then translated along the longitudinal member 120 into engagement around the upstanding arms 128 and 130. To do this, the inclined ridges 148 and 150 are slid so they project into the space between the upstanding arms 128 and 130. At that point, the component parts are assembled as illustrated in FIGS. 21 and 22 and are ready for implantation into a pedicle by the surgeon.

Figure 23:
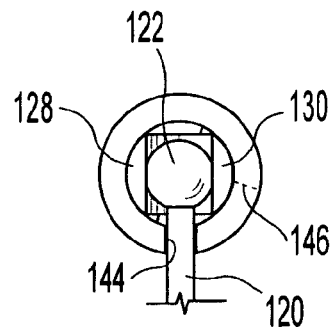
FIG. 23 is a top plan view of the assembled components of FIGS. 14-20 manipulated to a second configuration.
Figure 24:
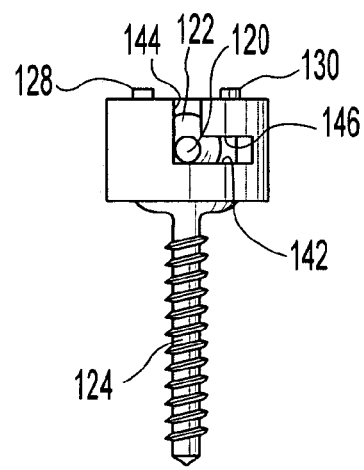
FIG. 24 is a front elevation of the assembled components of FIG. 23.
Figure 25:
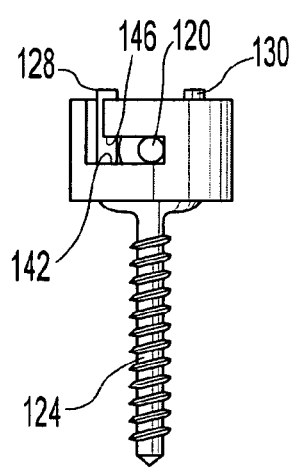
FIG. 25 is a front elevation of the assembled components of FIGS. 14-24 but being further manipulated into a third configuration.
Figure 26:
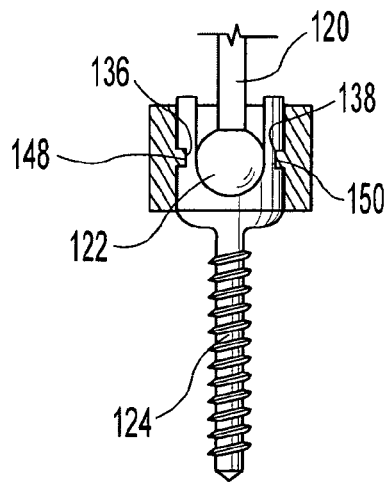
FIG. 26 is a frontal, sectional view of the assembled components configured as illustrated in FIG. 25.

After the assembled unit is implanted, the longitudinal member 120 is rotated toward the spine and into the axial segment 144 of the L-shaped slot 142 to the position illustrated in FIGS. 23 and 24 and also into engagement with an anchor joint formed on another pedicle screw. After the longitudinal member 120 is attached to the second pedicle screw, the collar 140 is rotated clockwise (to the left in the Figs.) as illustrated in FIGS. 25 and 26. The clockwise rotation causes the circumferential segment 146 of the L-shaped slot 14 to engage the longitudinal member 120 and trap it in position. The clockwise rotation also causes the inclined ridges 148 and 150 to slide into and along the inclined grooves 136 and 138. Because the ridges 148 and 150 are inclined, the collar 140 translates axially a small distance and is tightened in place in the manner of a screw being tightened into a nut. The ends of the inclined grooves 136 and 138 can be formed with ends that turn or are inclined in the opposite axial direction to provide a more positive lock.

While certain preferred embodiments of the present invention have been disclosed in detail, it is to be understood that various modifications may be adopted without departing from the spirit of the invention or scope of the following claims.

The invention claimed is:

1. A spinal implant for being surgically attached to and supporting at least two adjacent spinal vertebrae in stationery relationship, the implant comprising:
   (a) a longitudinal member attached by an articulation joint to a first pedicle screw, the longitudinal member being pivotable to extend in a cranial-caudal direction and attach to a second pedicle screw to join together the first pedicle screw and the second pedicle screw, the articulation joint being a universal joint, the articulation range of the articulation joint being through an angle extending at least from a 90° angle between the longitudinal axis of the first pedicle screw and the longitudinal axis of the longitudinal member to a coaxial orientation between said longitudinal axes to permit the first pedicle screw to be screwed into a pedicle of a first vertebra with the longitudinal member attached to the first pedicle screw;

(b) an articulation lock for securing the longitudinal member to the first pedicle screw in a selected orientation and preventing relative articulation from said selected orientation; and (c) a second pedicle screw for attachment in a pedicle of a second vertebra, the second pedicle screw having an anchor joint adapted and contoured for receiving and attaching to the longitudinal member after the longitudinal member is rotated into engagement with the anchor joint and the anchor joint also having an articulation lock for fixing the longitudinal member in a stationary, spatial relationship with the second pedicle screw wherein the articulation joint comprises a pivotable hinge having a bracket fixed to a top of the first pedicle screw, a rotatable hub fixed to the longitudinal member and a screw extending through the bracket and the hub for providing a pivot and for tightening the hub against the bracket.

2. A spinal implant for being surgically attached to and supporting at least two adjacent spinal vertebrae in stationery relationship, the implant comprising:

(a) a longitudinal member attached by an articulation joint to a first pedicle screw, the longitudinal member being pivotable to extend in a cranial-caudal direction and attach to a second pedicle screw to join together the first pedicle screw and the second pedicle screw, the articulation joint being a universal joint, the articulation range of the articulation joint being through an angle extending at least from a 90° angle between the longitudinal axis of the first pedicle screw and the longitudinal axis of the longitudinal member to a coaxial orientation between said longitudinal axes to permit the first pedicle screw to be screwed into a pedicle of a first vertebra with the longitudinal member attached to the first pedicle screw;

(b) an articulation lock for securing the longitudinal member to the first pedicle screw in a selected orientation and preventing relative articulation from said selected orientation; and (c) a second pedicle screw for attachment in a pedicle of a second vertebra, the second pedicle screw having an anchor joint adapted and contoured for receiving and attaching to the longitudinal member after the longitudinal member is rotated into engagement with the anchor joint and the anchor joint also having an articulation lock for fixing the longitudinal member in a stationary, spatial relationship with the second pedicle screw;

wherein the universal joint has a lower yoke fixed to a head of a pedicle screw, the lower yoke having two arms pivotally connected to a first pair of legs of an intermediate spider, the universal joint also having an upper yoke having an end with two arms having pivotal connections pivotally connected to a second pair of legs of the spider, the upper yoke being attached at an opposite end to a longitudinal member and wherein the pivotal connections on the yoke are formed by four threaded rods, each of the four threaded rods being fixed to a different one of the legs of the spider and each rod pivotally extends through a different one of the legs of the yokes and having nuts each threadedly engaged to a different one of threaded rods.

* * * * *